US00PP16592P2

(12) United States Plant Patent
Danziger

(10) Patent No.: US PP16,592 P2
(45) Date of Patent: May 30, 2006

(54) ***VERBENA* PLANT NAMED 'DANDON17'**

(50) Latin Name: ***Verbena* sp.**
Varietal Denomination: Dandon17

(75) Inventor: Gabriel Danziger, Moshav Nir-Zvi (IL)

(73) Assignee: Danziger "Dan " Flower Farm, Post Beit Dagan (IL)

( * ) Notice: Subject to any disclaimer, the term of this patent is extended or adjusted under 35 U.S.C. 154(b) by 0 days.

(21) Appl. No.: 11/057,208

(22) Filed: Feb. 15, 2005

(51) Int. Cl.
*A01H 5/00* (2006.01)

(52) U.S. Cl. ..... Plt./308

(58) Field of Classification Search ..... Plt./308
See application file for complete search history.

*Primary Examiner*—Anne Marie Grunberg
(74) *Attorney, Agent, or Firm*—Foley & Lardner, LLP

(57) ABSTRACT

A new and distinct *Verbena* plant named 'Dandon17' characterized by having semi-spread plant habit; vigorous and highly branched branching habit; wide, bright green leaves; large, single, cruciform red flowers making up a cluster with a relatively large white center; and early flowering response in spring and continuous flowering throughout summer.

2 Drawing Sheets

Botanical designation: *Verbena* sp.
Varierty denomination: 'Dandon17'.

BACKGROUND OF THE INVENTION

The present invention relates to a new and distinct cultivar of *Verbena* plant, botanically known as *Verbena* sp., hereinafter referred to by the cultivar name 'Dandon17'.

*Verbena*, of the Verbenaceae family, consists of a couple hundred perennials, some of which are semi-evergreens, that are native to North and South America. The present invention relates to a new and distinct perennial cultivar of *Verbena*.

The new *Verbena* cultivar is a product of a planned breeding program conducted by the inventor, Gabriel Danziger, in Moshav Mishmar Hashiva, Israel. The objective of the breeding program was to develop a new *Verbena* variety with red flowers with large white centers and broad leaves.

The new *Verbena* cultivar originated from a cross made in September 2002, by the inventor Gabriel Danziger, in Moshav Mishmar Hashiva, Israel. The female parent is designated 've-z-8' (unpatented). The male parent is open pollination. The new *Verbena* cultivar 'Dandon17' was discovered and selected by the inventor as a flowering plant within the progeny of the stated cross in a controlled environment in Moshav Mishmar Hashiva, Israel.

Asexual reproduction of the new *Verbena* cultivar by stem cutting was first performed in April of 2003 in Moshav Mishmar Hashiva, Israel, and has demonstrated that the combination of characteristics as herein disclosed for the new cultivar are firmly fixed and retained through successive generations of asexual reproduction. The new cultivar reproduces true-to-type.

BRIEF SUMMARY OF THE INVENTION

The following traits have been repeatedly observed and are determined to be unique characteristics of 'Dandon17' which in combination distinguish this *Verbena* as a new and distinct cultivar:

1. Semi-spread plant habit;
2. Vigorous and highly branched branching habit;
3. Wide, bright green leaves;
4. Large, single, cruciform red flowers making up a cluster with a relatively large white center; and
5. Early flowering response in spring and continuous flowering throughout summer.

Plants of 'Dandon17' differ from plants of the maternal parent in the characteristics described in Table 1:

TABLE 1

| Trait | New Cultivar | Female Parent |
|---|---|---|
| Plant habit | Semi - spread | Bushy |
| Flower size | Large petals and center | Medium size petals and small center |
| Flowering time | Late flowering relative to female | Earlier flowering time |

Of the many commercial cultivars known to the present inventor, the most similar in comparison to the new *Verbena* cultivar 'Dandon17' is the *Verbena* cultivar 'Tukana Scarlet' (unpatented). In side-by-side comparisons conducted in Moshav Mishmar Hashiva, Israel, plants of 'Dandon17' differed from plants of 'Tukana Scarlet' in the characteristics described in Table 2:

TABLE 2

| Trait | New Cultivar | Comparison Cultivar |
|---|---|---|
| Plant habit | Semi-spread | Spread |
| Flower Color | Darker red RHS 46B | Lighter red RHS 46C |
| Flower Center | Larger white center | Minute flower center |
| Flower Size | 24 mm diameter | 20 mm diameter |

BRIEF DESCRIPTION OF THE DRAWING

The accompanying colored photographs illustrate the overall appearance of the new *Verbena* cultivar 'Dandon17' showing the colors as true as is reasonably possible with colored reproductions of this type. Colors in the photographs may differ slightly from the color values cited in the detailed botanical description which accurately describe the color of the 'Dandon17'.

The first photograph shows a side view perspective of a typical flowering 'Dandon17' in a hanging basket at about 3 months old.

The second photograph shows a close-up view of a typical flower cluster of 'Dandon17', which has about 25 flowers per the cluster, measures about 20 mm in diameter, and shows the color of the flower is dark red towards the center with a lighter hue towards the outer petals and a significant white center.

DETAILED BOTANICAL DESCRIPTION

The new *Verbena* cultivar 'Dandon17' has not been observed under all possible environmental conditions. The phenotype of the new cultivar may vary significantly with variations in environment such as temperature, light intensity, and daylength, without any change in the genotype of the plant.

The aforementioned photographs, together with the following observations, measurements and values describe plants of the new *Verbena* cultivar 'Dandon17' as grown outdoors in Moshav Mishmar Hashiva, Israel, under conditions which closely approximate those generally used in commercial practice. The plants were grown outdoors when daytime temperatures ranged from 23–29° C. and when nighttime temperatures range from 18–25° C. The cultivar's soil mixture was given complete, balanced fertilizers at 200–250 ppm nitrogen. Starting at about 4 weeks after transplant, EC of 2.0 is optimum. The cultivar was produced in a 13 cm pot. After 9 weeks in total, the cultivar is ready for sale. The reaction time from day of induction to day of first opened flower is 7 days.

The photographs and descriptions were taken during the Autumn when outdoor day temperatures ranged from 17–23° C. and when nighttime temperatures ranged from 5–13° C. at night. The age of the plants described is 9 weeks old.

Color references are made to The Royal Horticultural Society Colour Chart (R.H.S.), published 2001, except where general colors of ordinary significance are used.

Classification:
- *Botanical.*—*Verbena* sp.

Parentage:
- *Female or seed parent.*—*Verbena* cultivar designated 've-z-8' (unpatented).
- *Male or pollen parent.*—Bulk pollen.

Propagation:
- *Type.*—Stem cutting.
- *Time and temperature to initiate roots.*—Summer: 5 to 7 days (25–28° C.). Winter: 8 to 10 days (15–20° C.).
- *Time and temperature to produce a rooted cutting or liner.*—Summer: 14 days (25–28° C.). Winter: 18 to 20 days (15–20° C.).
- *Rooting habit and description.*—Very long and fibrous.

Plant:
- *General appearance and form.*—Semi spread growth, with flowers in a cluster form, surrounded by high number of leaves.
- *Branching habit.*—Highly branched.
- *Growth habit.*—Medium.
- *Growth rate.*—Vigorous.
- *Plant height.*—15–20 cm.
- *Plant width* (*spread*).—60 cm.

Lateral branches:
- *Length.*—5–20 cm.
- *Diameter.*—2 mm.
- *Internode length.*—25–35 mm.
- *Strength.*—Strong, firm.
- *Texture.*—Pubescent.
- *Color.*—Upper surface: RHS 138B, green. Lower surface: RHS 138B, green.

Foliage:
- *Arrangement.*—Whorled.
- *Overall shape of leaf.*—Triangular (deltoid).
- *Shape at apex.*—Sharply pointed (acute).
- *Shape at base.*—Uneven.
- *Length.*—30–35 mm.
- *Width.*—30 mm.
- *Margin.*—Scalloped (crenate).
- *Texture.*—Upper surface: bullate (puberulous). Lower surface: lustrous (puberulous).
- *Color of mature* (*developed*) *leaf.*—Upper surface: RHS 147B, yellow-green. Lower surface: RHS 146B, yellow-green.
- *Color of immature* (*expanding*) *leaf:*—Upper surface: RHS 146A, yellow-green. Lower surface: RHS 146C, yellow-green.
- *Venation pattern.*—Palmate.
- *Venation color.*—Upper surface: RHS-148D, yellow-green. Lower surface: RHS-147B, yellow-green.
- *Petiole length.*5 mm.
- *Petiole diameter.*——1 mm.
- *Petiole color.*—RHS 144C, yellow-green.

FLOWER

Description:
- *Flower type and habit.*—Single, upright cruciform flowers arranged in clusters. The flowers are positioned above the foliage and are persistent.
- *Natural flowering season:*—Early flowering in spring and continuous flowering throughout summer. Season can be extended year round as long as the temperature is relatively high.
- *Time to flower.*—7 weeks.
- *Rate of flowers opening.*—About 10 flowers per week per cluster. It depends on the age of the plant. The younger the plant the less flowers, while an older plant products a lot more flowers. Therefore the range is between 5 to 20 clusters per week.
- *Quantity of flowers.*—About 15 to 27 per inflorescence.
- *Flower size.*—Diameter: 20 mm. Throat diameter: 1.5–2 mm. Tube diameter, at base: 1 mm. Tube length: 17 mm.
- *Post production longevity.*—About 8 to 12 days.
- *Fragrance* (*if any*).—None.

Inflorescence:
- *Inflorescence height.*—30 mm.
- *Inflorescence diameter.*—55 mm.

Buds:
- *Rate of opening* (*from showing color to fully open flower*).—96 hours.
- *Length.*—10 mm.
- *Diameter.*—At Apex: 6 mm. At Base: 3 mm.
- *Shape.*—Ovulate.
- *Color.*—Apex: RHS 44A, red. Base: RHS 47D, red.

Petals:

*Quantity and arrangement per flower.*—5, single.
*Lobe length.*—11 mm.
*Lobe width.*—7 mm.
*Overall shape.*—Cruciform.
*Shape at apex.*—Heart shaped.
*Margin.*—Smooth.
*Texture.*—Upper surface: smooth Lower surface: smooth.
*Color of opening petals.*—Upper surface: RHS 45A, red. Lower surface: RHS 45B, red.
*Color of fully opened petals.*—Upper surface: RHS 46B, red. Lower surface: RHS 46D, red.
*Fading.*—The color of the petals do not fade.

Sepals:

*Quantity and arrangement per flower.*—1 per flower.
*Length.*—10 mm.
*Width.*—2 mm.
*Overall shape.*—Tubular.
*Shape at apex.*—Star shaped.
*Margin.*—Entire.
*Texture.*—Upper surface: pubescent. Lower surface: pubescent.
*Color of sepals.*—Upper surface: RHS 143C, green. Lower surface: RHS 144D, green.

Peduncles:

*Appearance and angle.*—Straight, similar to the stem.
*Length.*—10 mm.
*Diameter.*—2 mm.
*Strength.*—Strong.
*Color.*—RHS 137D, green.

Reproductive organs:

Androecium:

*Stamen quantity of per flower.*—4.
*Stamen length.*—2 mm.
*Filament color.*—RHS 3D, yellow.
*Anther shape.*—Conical.
*Anther length.*—1 mm.
*Anther color.*—RHS 1B, yellow.
*Pollen amount.*—Plentiful.
*Pollen color.*—RHS 1B, yellow.
*Requirement for pollination* (*if any*).—None. In Israel, the reproductive organs are receptive all year round both indoors and outdoors.

Gynoecium:

*Pistil quantity of per flower.*—1.
*Pistil length.*—15 mm.
*Stigma shape.*—Circular.
*Stigma color.*—RHS 143C, green.
*Style length.*—14 mm.
*Style color.*—RHS 154C, yellow-green.
*Ovary color.*—RHS 144C, yellow-green.

Seeds:

*Quantity.*—2 to 4:
*Length.*—4 mm.
*Diameter.*—1 mm.
*Texture.*—Hairless but not smooth.
*Color.*—Greyed-orange, RHS 177A.

Fruit: None observed.

Disease/pest resistance: Low; none observed.

Disease/pest susceptibility: Good, not susceptible to powdery mildew and Alternaria in our examinations.

Growth retardants used: None used.

Temperature tolerance: Frost tender: temperatures below 5° C. may damage plant.

I claim:

1. A new and distinct *Verbena* plant named 'Dandon17', substantially as illustrated and described herein.

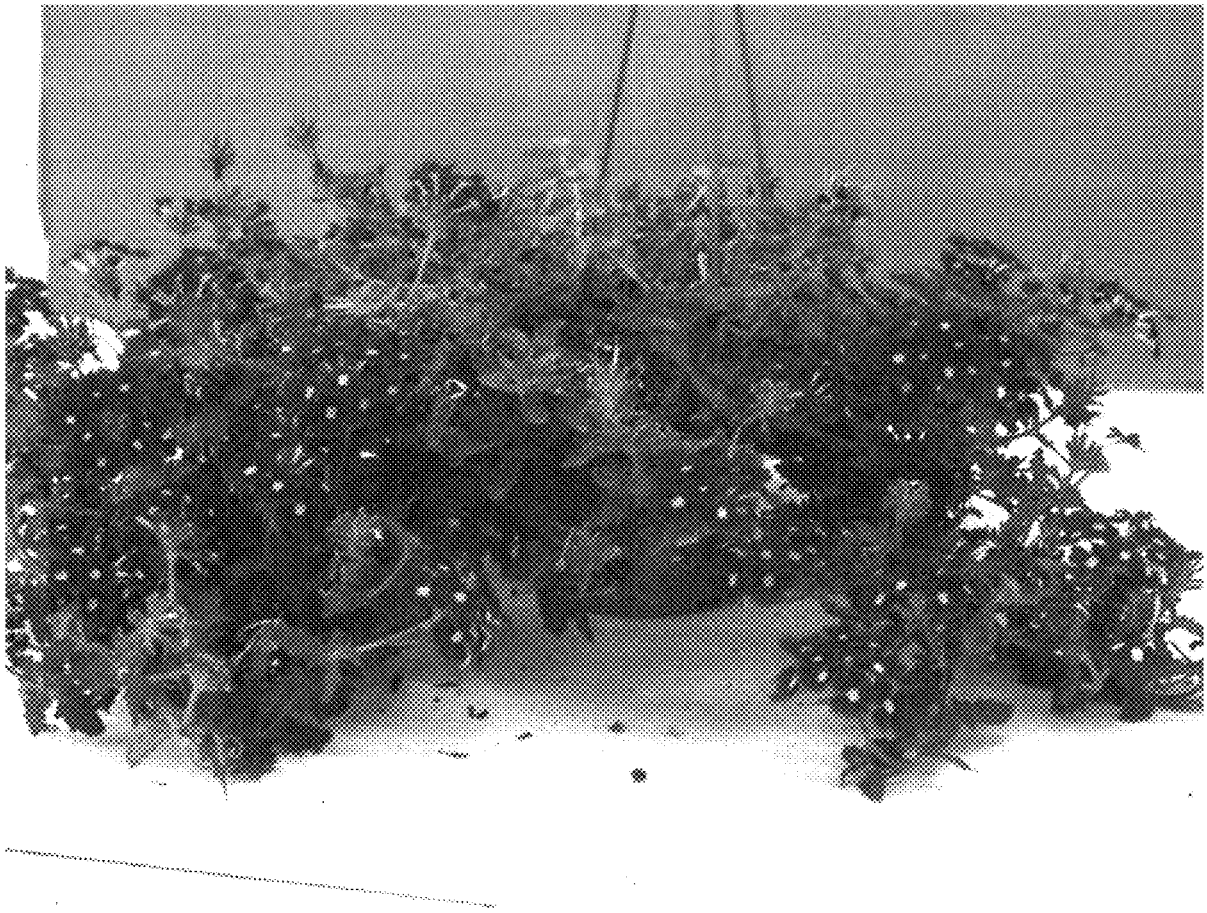

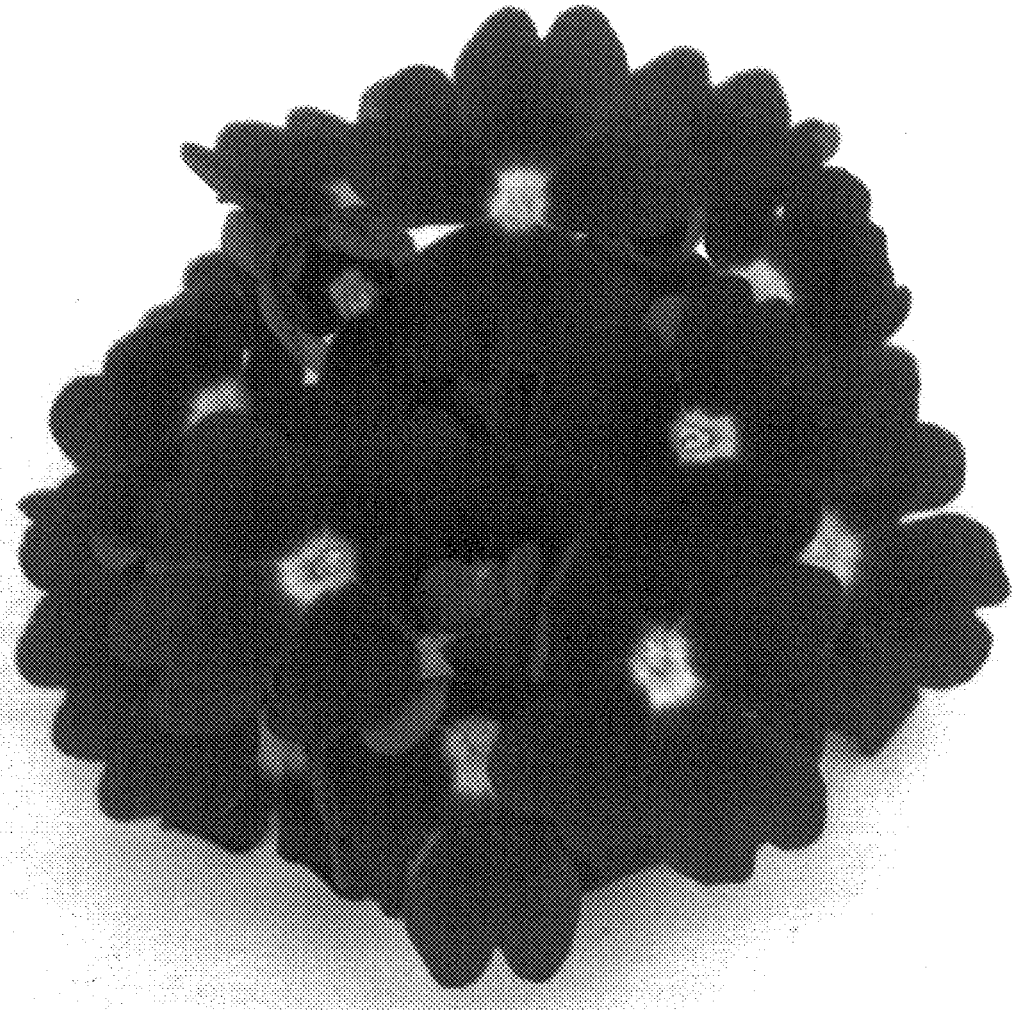

* * * * *